(12) United States Patent
Goldenberg et al.

(10) Patent No.: US 8,083,691 B2
(45) Date of Patent: Dec. 27, 2011

(54) APPARATUS AND METHOD FOR SENSING FORCE

(75) Inventors: Alex S. Goldenberg, San Francisco, CA (US); Randall L. Schlesinger, San Mateo, CA (US); Eric A. Schultheis, Los Altos, CA (US)

(73) Assignee: Hansen Medical, Inc., Mountain View, CA (US)

( * ) Notice: Subject to any disclaimer, the term of this patent is extended or adjusted under 35 U.S.C. 154(b) by 464 days.

(21) Appl. No.: 12/269,684

(22) Filed: Nov. 12, 2008

(65) Prior Publication Data

US 2010/0121138 A1    May 13, 2010

(51) Int. Cl.
  *A61B 5/103*  (2006.01)
  *A61B 5/117*  (2006.01)
(52) U.S. Cl. ........................................... 600/587
(58) Field of Classification Search .......... 600/587–595; 606/130
  See application file for complete search history.

(56) References Cited

U.S. PATENT DOCUMENTS

| | | | | |
|---|---|---|---|---|
| 4,815,476 A * | 3/1989 | Clossick | ........................ | 600/564 |
| 5,318,525 A * | 6/1994 | West et al. | ................... | 604/95.04 |
| 5,766,196 A * | 6/1998 | Griffiths | .......................... | 606/170 |
| 5,911,694 A * | 6/1999 | Ikeda et al. | ..................... | 600/587 |
| 6,068,604 A * | 5/2000 | Krause et al. | .................. | 600/587 |
| 6,726,699 B1 * | 4/2004 | Wright et al. | .................. | 606/185 |
| 2003/0055360 A1 * | 3/2003 | Zeleznik et al. | .............. | 600/587 |
| 2004/0254566 A1 * | 12/2004 | Plicchi et al. | ....................... | 606/1 |
| 2005/0222554 A1 | 10/2005 | Wallace et al. | | |
| 2005/0250989 A1 * | 11/2005 | Suzuki | .......................... | 600/106 |
| 2006/0095022 A1 | 5/2006 | Moll et al. | | |
| 2006/0276775 A1 | 12/2006 | Rosenberg et al. | | |
| 2007/0043338 A1 | 2/2007 | Moll et al. | | |
| 2007/0156123 A1 | 7/2007 | Moll et al. | | |
| 2007/0197896 A1 | 8/2007 | Moll et al. | | |
| 2007/0233044 A1 | 10/2007 | Wallace et al. | | |

FOREIGN PATENT DOCUMENTS

EP        1285634 A1 *   2/2003

\* cited by examiner

*Primary Examiner* — Max Hindenburg
*Assistant Examiner* — Rene Towa
(74) *Attorney, Agent, or Firm* — Vista IP Law Group LLP (57) ABSTRACT

A medical system comprises a medical probe including an elongated probe body, a lumen extending within the probe body, an axially flexible section, and a push-pull rod slidably disposed within the lumen. The system comprises a ditherer mechanically coupled to the rod for cyclically displacing it axially back and forth within the lumen, such that the ends of the probe body are axially displaced relative to each other via the axially flexible section. The system further comprises a sensor for sensing a force axially applied to the distal end of the probe body. A method comprises introducing a medical probe into a patient, axially dithering the distal end of the medical probe back and forth relative to the proximal end of the medical probe, and sensing a force applied between tissue of the patient and the distal end of the medical probe while the distal end is axially dithered.

14 Claims, 8 Drawing Sheets

APPARATUS AND METHOD FOR SENSING FORCE

FIELD OF INVENTION

The invention relates generally to minimally-invasive instruments and systems, such as manually or robotically steerable catheter systems, and more particularly to steerable catheter systems for performing minimally invasive diagnostic and therapeutic procedures.

BACKGROUND

Minimally invasive procedures are preferred over conventional techniques wherein the patient's body cavity is open to permit the surgeon's hands access to internal organs. Thus, there is a need for a highly controllable yet minimally sized system to facilitate imaging, diagnosis, and treatment of tissues which may lie deep within a patient, and which may be accessed via naturally-occurring pathways, such as blood vessels, other lumens, via surgically-created wounds of minimized size, or combinations thereof.

Currently known minimally invasive procedures for the treatment of cardiac and other disease conditions use manually or robotically actuated instruments, which may be inserted transcutaneously into body spaces such as the thorax or peritoneum, transcutaneously or percutaneously into lumens such as the blood vessels, through natural orifices and/or lumens such as the mouth and/or upper gastrointestinal tract, etc.

When controlling an elongate instrument, such as a catheter, in any one of these applications, the physician operator can push on the proximal end of the catheter and attempt to feel the distal end make contact with pertinent tissue structures, such as the walls of the heart. Some experienced physicians attempt to determine or gauge the approximate force being applied to the distal end of a catheter due to contact with tissue structures or other objects, such as other instruments, prostheses, or the like, by interpreting the loads they tactically sense at the proximal end of the inserted catheter with their fingers and/or hands. Such an estimation of the force, however, is quite challenging and somewhat imprecise given the generally compliant nature of many minimally-invasive instruments, associated frictional loads, dynamic positioning of the instrument versus nearby tissue structures, and other factors.

Manually and robotically-navigated interventional systems and devices, such as steerable catheters, are well suited for performing a variety of minimally invasive procedures. Manually-navigated catheters generally have one or more handles extending from their proximal end with which the operator may steer the pertinent instrument. Robotically-navigated catheters may have a proximal interface configured to interface with a catheter driver comprising, for example, one or more motors configured to induce navigation of the catheter in response to computer-based automation commands, commands input by the operator at a master input device, combinations thereof, or the like.

Regardless of the manual or electromechanical nature of the driving mechanism for a diagnostic or interventional catheter, the operator performing the procedure would prefer to have accurate, timely information regarding the forces experienced at the distal portion of the catheter. There, thus, is a need for an improved force-sensing technology to facilitate the execution of minimally-invasive interventional procedures. It is desirable to have the capability to accurately monitor the loads applied by or to the catheter from adjacent tissues and other objects.

SUMMARY OF THE INVENTION

In accordance with one aspect of the present inventions, a medical system comprises a medical probe, a dithering mechanism, and at least one sensor. The medical probe includes an elongated probe body (e.g., an intravascular catheter body) having a proximal section, a distal section, and an axially translatable section between the proximal and distal sections, a lumen axially extending within the probe body, and an axially translatable section disposed between the proximal and distal sections of the probe body. In one embodiment, the axially translatable section of the probe body comprises an axially flexible member (e.g., a bellows). In another embodiment, the axially translatable section of the probe body comprises at least one seal that allows one of the proximal and distal sections of the probe body to slide within the other of the proximal and distal sections of the probe body.

The medical probe further comprises a push-pull rod slidably disposed within the lumen, with the distal end of the push-pull rod being affixed to the probe body at a point distal to the axially flexible section (e.g., at the distal end of the probe body) and the proximal end of the push-pull rod extending from the proximal end of the probe body. In one embodiment, the medical probe further comprises a coil wrapped around the push-pull rod, with the coefficient of friction between the coil and the lumen being less than the coefficient of friction between the push-pull rod and the lumen. The medical system may further include an operative medical element mounted to the distal section of the probe body.

The dithering mechanism is mechanically coupled to the proximal end of the push-pull rod, and is configured for cyclically displacing the push-pull rod axially back and forth within the lumen of the probe body, such that the proximal and distal sections of the probe body are axially displaced relative to each other via the axially translatable section. The sensor(s), which in one embodiment, may be mounted to the ditherer, are configured for sensing an external force axially applied to the distal tip of the probe body.

In one embodiment, the medical system further comprises a drive mechanism affixed to the proximal section of the probe body for effecting movement of the probe body within at least one degree of freedom. The medical probe may further include at least one control element (e.g., a steering wire) extending within the probe body, in which case, the drive mechanism may include an adapter coupled to the control element(s) for deflecting the distal tip of the probe body in at least one direction. The control element(s) may be affixed to the probe body at a point proximal to the axially translatable section. The push-pull rod may be configured for being axially displaced by the ditherer relative to the drive mechanism. If the medical system comprises an introducer sheath having a lumen in which the probe body is disposed, the drive mechanism may be configured for axially displacing the probe body and the introducer sheath relative to each other.

In another embodiment, the medical system further comprises a computer configured for obtaining a baseline force measurement by receiving signals from the force sensor(s) when the push-pull rod is dithered back and forth without an external axial force applied to the distal tip of the probe body, for obtaining a total force measurement by receiving signals from the force sensor(s) when the push-pull rod is dithered back and forth with an external axial force applied to the distal tip of the probe body, and computing the external axial force applied to the distal tip of the probe body by subtracting the baseline force measurement from the total force measurement.

In accordance with another aspect of the present inventions, a medical method is provided. The method comprises introducing a medical probe having an elongated probe body into a patient (e.g., intravascularly), axially dithering the distal end of the probe body back and forth relative to the proximal end of the probe body, and sensing a force applied between tissue of the patient and the distal end of the probe body while the distal end of the probe body is axially dithered.

In one method, the medical probe is operated to perform a therapeutic or diagnostic function on the patient. Another method comprises robotically controlling movement of the medical probe within at least one degree of freedom (e.g., deflecting the distal end of the medical probe in at least one direction). In still another method, the force applied between the tissue and the distal end of the probe body may be measured by obtaining a baseline force measurement when the distal end of the probe body is axially dithered back and forth without an external axial force axially applied between the tissue and the distal end of the probe body, obtaining a total force measurement when the distal end of the probe body is dithered back and forth with the external axial force axially applied between the tissue and the distal end of the probe body, and subtracting the baseline force measurement from the total force measurement.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of various embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE ILLUSTRATED EMBODIMENTS

Before describing specific embodiments in detail, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, introducers or other surgical tools for performing minimally invasive surgical procedures.

As used in this specification and the appended claims, the singular forms "a," "an" and "the" include plural referents unless the context clearly dictates otherwise. Thus, for example, the term "a member" is intended to mean a single member or a combination of members, "a fluid" is intended to mean one or more fluids, or a mixture thereof. Furthermore, the words "proximal" and "distal" refer to direction close to and away from, respectively, an operator (e.g., surgeon, physician, nurse, technician, etc.) who would insert the medical device into the patient, with the tip-end (i.e., distal end) of the device inserted inside a patient's body first. Thus, for example, the catheter end inserted inside the patient's body would be the distal end of the catheter, while the catheter end left outside the patient's body would be the proximal end of the catheter.

Before describing an embodiment of a robotic catheter system constructed in accordance with the present inventions, it may be helpful to first describe one robotic catheter system that has been previously designed to sense force. U.S. patent application Ser. No. 11/678,001 (the '001 application), which is commonly assigned with the present application, discloses robotically-navigated interventional systems and methods having the capability to sense force between a distal end of a working instrument (such as a catheter) and the surface of a body cavity or lumen (referred to collectively as a "body space"). The robotic system not only detects contact between the working instrument and the surface, but also measures the magnitude of the force, also called the load. Such systems and methods can also be used to detect contact with tissue structures.

The robotic system described in the '001 application comprises a robotic instrument driver that directly interfaces with a coaxial arrangement of an introducer sheath and a guide catheter, and an operator control station for remotely controlling movements of the introducer sheath and guide catheter through the instrument driver. A working catheter, which can be manually operated by a physician, is disposed through the robotic guide catheter (typically via a Touhy valve), which in turn, is disposed through the robotic introducer sheath. The instrument driver comprises two actuation mechanisms (referred to as "splayers") that tension control wires within the introducer sheath and guide sheath to provide them with steering actuation. The instrument driver may move the splayers relative to each other to provide independent insertion or retraction movements to the introducer sheath and guide catheter along a longitudinal axis.

The robotic system described in the '001 application measures a force applied to the distal end of the working catheter using a dithering technique. In particular, the working catheter is "dithered" with respect to the guide catheter by moving the guide catheter back and forth in a repeated cyclic motion to overcome frictional challenges, normally complicating a measurement of loads at the distal end of the working catheter when in contact with a surface. That is, if a user were to position the working catheter down the lumen of the guide catheter, so that the distal end of the working catheter extends out slightly beyond the distal end of the guide catheter, it may be difficult to accurately sense force applied to the distal end of the working catheter due to the complications of the physical relationship with the associated guide catheter. In particular, in a steady state wherein there is little or no relative axial or rotational motion between the working catheter and the guide catheter, the static coefficient of friction is applicable, and as such, there are relatively large frictional forces keeping the working catheter in place relative to the guide catheter (no relative movement between the two). To release this relatively tight coupling and facilitate proximal measurement of forces applied to the distal end of the working catheter, the dithering motion is used to effectively break loose this frictional coupling.

The dithering motion is provided by a ditherer that is mechanically coupled to the proximal end of the working catheter extending out from the proximal end of the guide catheter. A bellows is provided on the Touhy valve through which the working catheter is inserted into the guide catheter to facilitate dithering of the working catheter. Sensors are provided on the ditherer for measuring forces applied at the distal end of the working catheter and transmitted through the shaft of the working catheter to the ditherer. The dynamic friction is baselined by measuring the insertion and withdrawal forces generated by the moving working catheter. Thus, any additional force that is measured by the application of external forces to the distal end of the working catheter can be calculated by subtracting the baseline frictional force from the total measured force.

Thus, the specific dithering technique discussed in the '001 application provides an accurate technique for sensing forces applied to the distal end of a manually operated working catheter. The embodiment disclosed herein provides a dithering technique for sensing forces applied to the distal end of a robotic working catheter (e.g., a robotically steerable catheter having a therapeutic and/or diagnostic function) despite the fact that the proximal end of the working catheter would be affixed to a robotically controlled actuator, such as a splayer.

Figure 1:
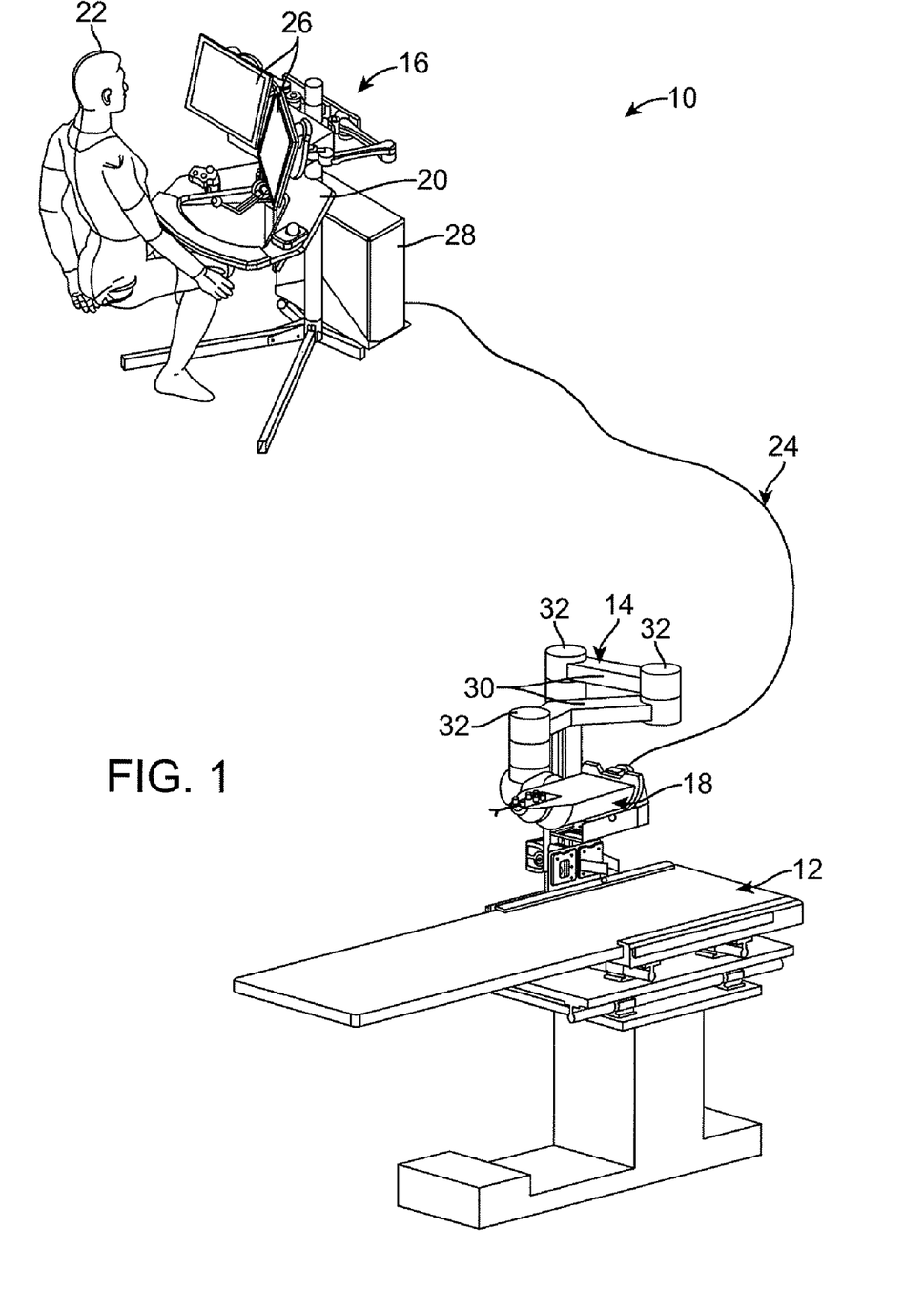
FIG. 1 is a perspective view of a medical robotic system constructed in accordance with one embodiment of the present inventions.

Referring to FIG. 1, one embodiment of a robotic catheter system 10 constructed in accordance with the present invention will now be described. The system 10 generally comprises an operating table 12 having a movable support-arm assembly 14, an operator control station 16 located remotely from the operating table 12, and a robotic catheter assembly 18 mounted to the support-arm assembly 14 above the operating table 12. Exemplary robotic catheter systems that may be modified for constructing and using embodiments of the present invention are disclosed in detail in the following U.S. patent applications, which are all expressly incorporated herein by reference in their entirety: U.S. patent application Ser. No. 11/678,001, filed Feb. 22, 2007; U.S. patent application Ser. No. 11/073,363, filed Mar. 4, 2005; U.S. patent application Ser. No. 11/179,007, filed Jul. 6, 2005; U.S. patent application Ser. No. 11/418,398, filed May 3, 2006; U.S. patent application Ser. No. 11/481,433, filed Jul. 3, 2006; U.S. patent application Ser. No. 11/637,951, filed Dec. 11, 2006; U.S. patent application Ser. No. 11/640,099, filed Dec. 14, 2006; U.S. Patent Application Ser. No. 60/833,624, filed Jul. 26, 2006; and U.S. Patent Application Ser. No. 60/835,592, filed Aug. 3, 2006.

The control station 16 comprises a user interface 20 that is operatively connected to the robotic catheter assembly 18. A physician or other user 22 may interact with the user interface 20 to operate the robotic catheter assembly 18. The user interface 20 is connected to the robotic catheter assembly 18 via a cable 24 or the like, thereby providing one or more communication links capable of transferring signals between the control station 16 and the robotic catheter assembly 18. Alternatively, the user interface 20 may be located in a geographically remote location and communication is accomplished, at least in part, over a wide area network such as the Internet. The user interface 20 may also be connected to the robotic catheter assembly 18 via a local area network or even wireless network that is not located at a geographically remote location.

The control station 16 also comprises one or more monitors 26 used to display various aspects of the robotic instrument system 10. For example, an image of the introducer sheath and working catheter (described in further detail below) may be displayed in real time on the monitors 26 to provide the physician 22 with the current orientation of the various devices as they are positioned, for example, within a body lumen or region of interest. The control station 16 further comprises a computer 28, which may comprise a personal computer or other type of computer work station for performing the data processing operations disclosed herein.

The support-arm assembly 14 is configured for movably supporting the robotic catheter assembly 18 above the operating table 12 to provide convenient access to the desired portions of the patient (not shown) and provide a means to lock the catheter assembly 18 into position subsequent to the preferred placement. In this embodiment, the support-arm assembly 14 comprises a series of rigid links 30 coupled by electronically braked joints 32, which prevent joint motion when unpowered, and allow joint motion when energized by the control station 16. In an alternative embodiment, the rigid links 30 may be coupled by more conventional mechanically lockable joints, which may be locked and unlocked manually using, for example, locking pins, screws, or clamps. The rigid links 30 preferably comprise a light but strong material, such as high-gage aluminum, shaped to withstand the stresses and strains associated with precisely maintaining three-dimensional position of the weight of the catheter assembly 18.

Figure 2:
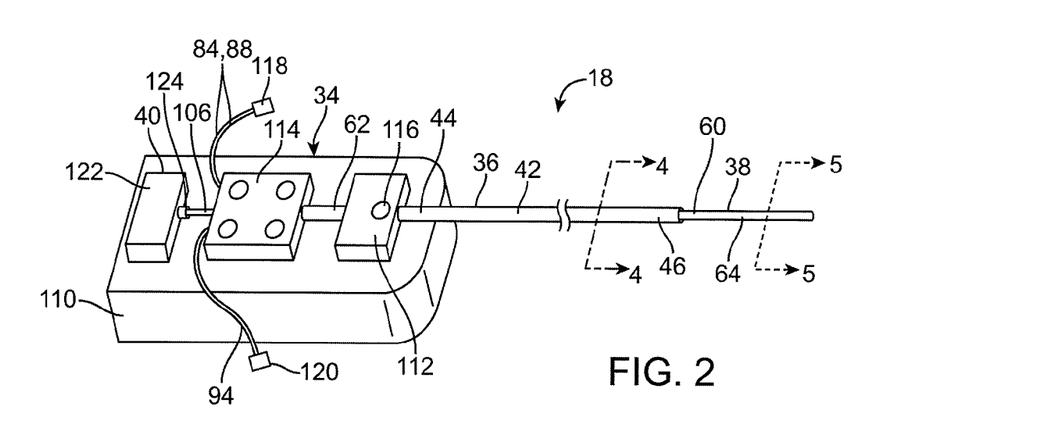
FIG. 2 is a perspective view of a robotic catheter assembly used in the medical robotic system of FIG. 1.
Figure 3:
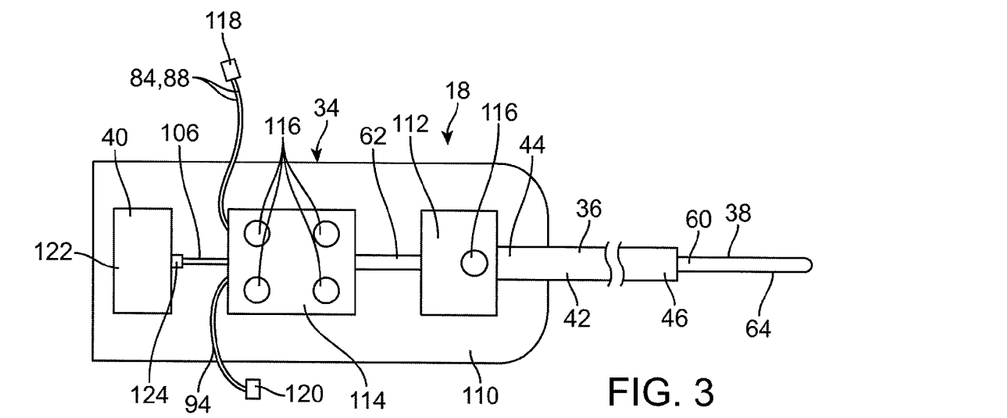
FIG. 3 is a top view of the robotic catheter assembly of FIG. 2.

Referring further to FIGS. 2 and 3, the robotic catheter assembly 18 will now be described in detail. The catheter assembly 18 comprises a robotic instrument driver 34, a robotic introducer sheath 36 and a robotic working catheter 38 mounted to the instrument driver 34 in a coaxial relationship, and a dithering force sensing assembly 40 mounted to the instrument driver 16 in mechanical communication with the proximal end of the working catheter 38. The robotic catheter assembly 18 may also include a drape (not shown) that covers the instrument driver 34.

Figure 4:
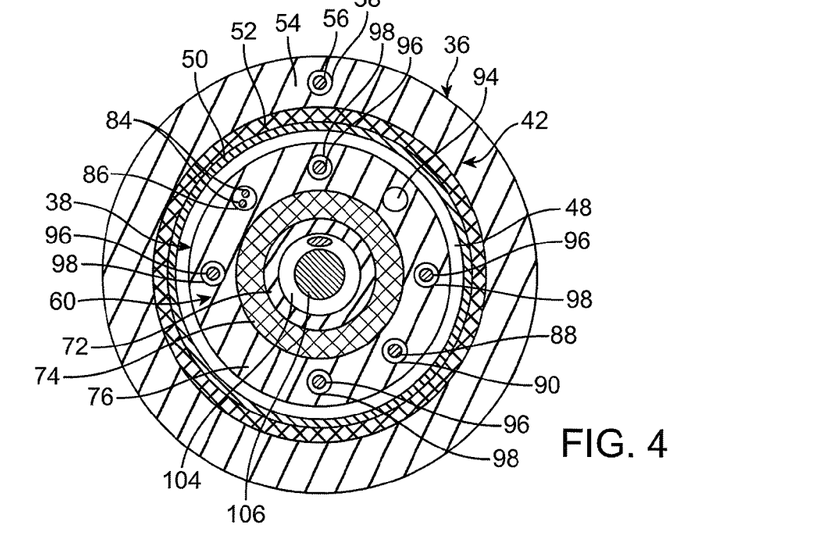
FIG. 4 is a cross-sectional view of the combination of an introducer sheath and working catheter used in the robotic catheter assembly of FIG. 2, particularly taken along the line 4-4.

Referring further to FIG. 4, the introducer sheath 36 comprises an elongated sheath body 42 having a proximal end 44 and a distal end 46, and a working lumen 48 extending through the sheath body 42 between the proximal and distal ends 44, 46. The geometry and size of the working lumen 48 will be selected in accordance with the cross-sectional geometry and size of the working catheter 38. The sheath body 42 may be composed of a low-friction inner layer 50 (e.g., a coating of silicone or polytetrafluoroethylene) to provide a low-friction surface to accommodate movement of the working catheter 38 within the working lumen 48, a stiffening layer 52 (e.g., a braided material or a metallic spine) disposed over the outer surface of the inner layer 50, and an outer layer 54 disposed over the outer surface of the stiffening layer 52.

The introducer sheath 36 further comprises a control element in the form of steering wire 56 extending through a steering lumen 58 disposed within the wall of the sheath body 42, and in particular, the outer layer 54. The distal end of the steering wire 56 is suitably mounted to an anchoring element (not shown) at the distal end 46 of the sheath body 42, and the proximal end of the steering wire 56 extends out the proximal end 44 of the sheath body 42, so that it can be suitably coupled to instrument driver 34, as discussed in further detail below. In the illustrated embodiment, the proximal end 44 of the sheath body 42 includes an aperture (not shown) through which the steering wire 56 exits to the instrument driver 34. Thus, it can be appreciated that the distal end 44 of the sheath body 42 can be alternately deflected and straightened via actuation of the steering wire 56.

The working catheter 38 may include any number of types of catheters, but in the illustrated embodiment, takes the form of an electrophysiology/ablation catheter. The forces sensed at the distal end of the catheter can be conveyed to an ablation generator (not shown). In this case, the ablation generator may be operated as long as the sensed force is with the range required to provide effective treatment. Alternatively, the ablation generator may automatically cease conveying ablation energy to the catheter if the sensed force falls outside of this requirement range. Optionally, the ablation generator may automatically compute and set and particular ablation power, ablation time, temperature, etc., as a function of the sensed force. It should be noted that the working catheter 38 may alternatively or additionally carry other types of operative elements, such as a tool or device (also called end effectors) (e.g. an imaging device or cutting tool disposed on the distal end of the catheter 38). It should also be noted that, although the working catheter 38 is described as an intravascular catheter, other types of medical probes may be used. For example, the working catheter 38 may take the form of an endoscopic surgical instrument or other elongated medical instrument. If not used intravascularly, the working catheter 38 can be rigid or semi-rigid.

The working catheter 38 passes through the lumen 48 of the introducer sheath 36, and is thus, moveable relative thereto. As shown in FIGS. 2 and 3, the working catheter 38 projects distally with respect to the distal end 44 of the sheath body 42. Of course, the working catheter 38 may be withdrawn proximally such that its distal end is substantially flush with the distal end 44 of the sheath body 42, or withdrawn proximally even further such that its distal end is disposed within the distal end 44 of the sheath body 42. The working catheter 38 may be movably positioned within the working lumen 48 of the introducer sheath 36 to enable relative insertion of the two devices, relative rotation, or "roll" of the two devices, and relative steering or bending of the two devices relative to each other, particularly when the distal end of the working catheter 38 is inserted beyond the distal tip of the introducer sheath 36.

Figure 5:
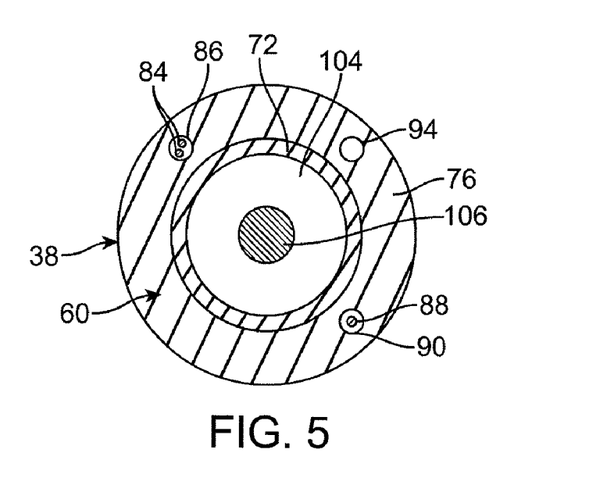
FIG. 5 is a cross-sectional view of the working catheter used in the robotic catheter assembly of FIG. 2, particularly taken along the line 4-4.
Figure 6:
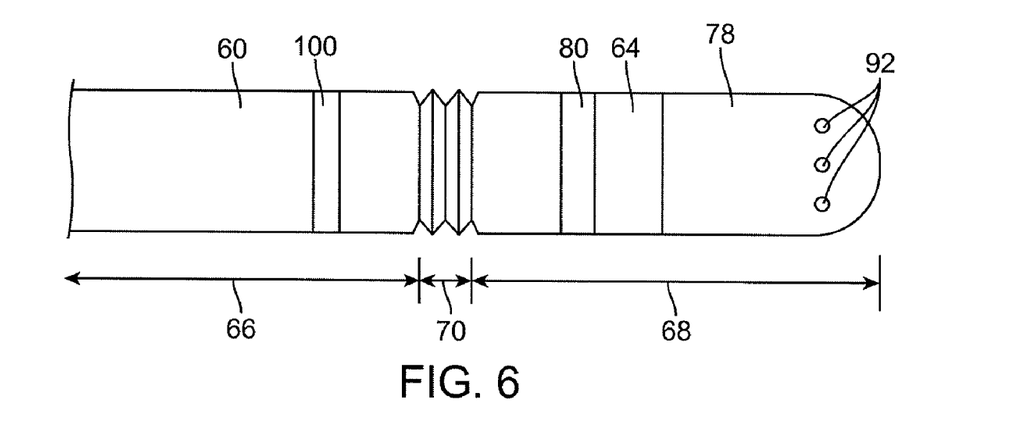
FIG. 6 is a plan view of the distal end of the working catheter used in the robotic catheter assembly of FIG. 2.
Figure 7:
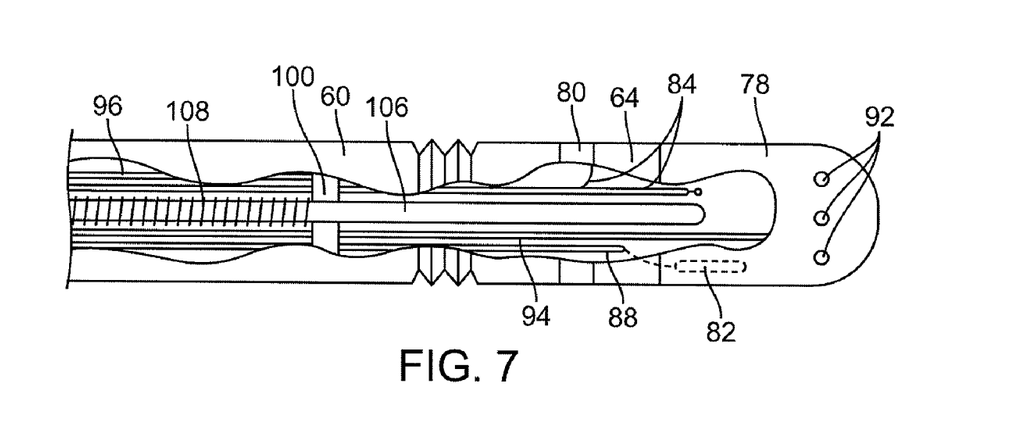
FIG. 7 is a partially cut-away view of the distal end of the working catheter used in the robotic catheter assembly of FIG. 2.

Referring further to FIGS. 6 and 7, the working catheter 38 comprises an elongated catheter body 60 having a proximal end 62 and a distal end 64. With respect to its composition, the catheter body 60 can be divided into three sections: a proximal shaft section 66, a distal section 68, and an axially flexible section 70 between the proximal and distal sections 66, 68. As best shown in FIG. 4, the proximal section 66 of the catheter body 60 may be composed of a low-friction inner lubricious layer 72, a stiffening layer 74 (e.g., a braided material or a metallic spine) disposed over the outer surface of the inner layer 72, and an outer layer 76 disposed over the outer surface of the stiffening layer 74. Because the proximal section 66 is structurally reinforced by inclusion of the stiffening layer 74, torque transmission and insertability of the catheter 38 is enhanced, while also providing enough cantilever bendability to facilitate access to remote tissue locations, such as the chambers of the heart. As best shown in FIG. 5, the distal section 68 of the catheter body 60 is composed of the inner lubricious layer 72 and the outer layer 76, and is more laterally flexible than the proximal section 66 due to the lack of a stiffening layer.

Significantly, the axially flexible section 70 of the catheter body 60, which in the illustrated embodiment takes the form of a bellows, can axially elongate and contract in much the same way as an accordion, thereby allowing the distal section 68 to be axially displaced relative to the proximal section 66 in response to the application of an axial force to the distal section 68. As will be described in further detail below, this feature allows the distal end 64 of the catheter body 60 to be axially dithered back and forth, while also facilitating the transfer of axial forces externally applied to the distal end 64 of the catheter body 60 to the force sensing assembly 40.

As briefly discussed above, the working catheter 38 takes the form of an electrophysiology/ablation catheter, and thus, comprises an ablation electrode, and in particular, a tip electrode 78, and an electrophysiology mapping electrode, and in particular, a ring electrode 80 mounted around the distal end 64 of the catheter body 60 proximal to the tip electrode 78. The electrodes 78, 80 may be composed of a suitably electrically conductive material, such as stainless steel or platinum. The catheter may further comprise a temperature sensor 82 (shown in phantom), such as a thermocouple or thermistor, suitably mounted within the tip electrode 78.

The catheter 38 comprises electrical leads 84 extending through a wire lumen 86 (shown in FIGS. 4 and 5) within the catheter body 60, with the distal ends of the electrical leads 84 respectively terminating at the tip electrode 78 and ring electrode 80, and the proximal ends of the electrical leads 84 terminating in the instrument driver 34 (described in further detail below). The catheter 38 also comprises an electrical lead 88 extending through a wire lumen 90 (shown in FIGS. 4 and 5) within the catheter body 60, with the distal end of the electrical lead 88 terminating at the temperature sensor 82, and the proximal end of the electrical lead 88 terminating in the instrument driver 34 (described in further detail below). The tip electrode 78 optionally includes fluid irrigation ports 92 through which a fluid, such as saline, can flow. In this case, the catheter 38 comprises a fluid lumen 94 extending through the catheter body 60, with the distal end of the fluid lumen 94 terminating within the tip electrode 78 in fluid communication with the irrigation ports 92, and the proximal end of the fluid lumen 94 terminating in the instrument driver 34 (described in further detail below).

The catheter 38 further comprises a plurality of control elements (in this case, four) in the form of steering wires 96 extending through respective steering lumens 98 disposed within the wall of the catheter body 60, and in particular, the outer layer 76 of the proximal section 66. The catheter 38 further comprises an anchoring element 100, and in particular an anchoring ring, embedded within the outer layer 76 of the proximal section 66 of the catheter body 60. The distal ends of the steering wires 96 (only one shown in FIG. 7) are suitably mounted to the anchoring ring 100, and the proximal end of the steering wires extend out the proximal end 62 of the catheter body 60, so that it can be suitably coupled to instrument driver 34 (described in further detail below). In the illustrated embodiment, the proximal end 62 of the catheter body 60 includes apertures (not shown) through which the respective steering wires 96 exit to the instrument driver 34. Thus, it can be appreciated that the distal end 64 of catheter body 60 can be alternately deflected in four different directions and straightened via actuation of the steering wires 96.

The catheter 38 further comprises a central lumen 104 extending within the catheter body 60 between the proximal and distal ends 62, 64 of the catheter body 60, and a push-pull rod 106 slidably disposed within the central lumen 104. The distal end of the push-pull rod 106 is affixed to the catheter body 60 at a point distal to the axially flexible section 70, and in particular, to the distal end 64 of the catheter body 60 (e.g., by soldering it to the inner surface of the tip electrode 78). The proximal end of the push-pull rod 106 extends out from the proximal end 62 of the catheter body 60, so that it can be suitably coupled to the force sensing assembly 40, as will be described in further detail below. In one embodiment, the push-pull rod 106 may also function as a "safety wire" to protect the patient if the distal shaft section 68 of the catheter body 60. The push-pull rod 106 may also be used as an electrical lead 84 in lieu of the electrical leads 84 discussed above. In this case, the push-pull rod 106 preferably includes an electrically conductive core and an electrically insulative coating disposed over the core.

The catheter 38 optionally comprises a coil 108 affixed around the push-pull rod 106. The coil 108 may be composed of a material or be coated with a material that has a lower coefficient of friction than that of the push-pull rod 106. For example, the coil 108 may be coated with polytetrafluoroethylene. In this manner, friction between the push-pull rod 106 and the lumen 104, which may otherwise be excessive if too much surface area of the push-pull rod 106 is in contact with the central lumen 104 when the proximal shaft section 66 is articulated in response to actuation of one of the steering wires 96, is reduced. The coil 108 also facilitates the centering of the push-pull rod 106 within the lumen 104.

Referring back to FIGS. 2 and 3, the instrument driver 34 provides robotic steering actuation, as well as robotic insertion and retraction actuation, to the introducer sheath 36 and working catheter 38 in accordance with control signals transmitted from the control station 16 (shown in FIG. 1). In particular, the instrument driver 34 comprises a housing 110 that contains motors (not shown), an introducer sheath adapter 112 ("sprayer") to which the proximal end 44 of the sheath body 42 is operably mounted, and a working catheter adapter 114 ("splayer") to which the proximal end 62 of the catheter body 60 is operably mounted.

The respective adapters 112, 114 are mechanically interfaced to the housing 110 in such a manner that they may be axially displaced relative to each other via operation of the motors, thereby effecting insertion or retraction movements of the respective introducer sheath 36 and working catheter 38 relative to each other, and thus, relative to the operating table 12 (shown in FIG. 1). Each of the adapters 112, 114 also comprise one or more rotating spools or drums 116 that can selectively tension or release the steering wires 56, 96 disposed within the respective sheath body 42 and catheter body 60, thereby effecting deflection of the distal ends 46, 64 of the sheath and catheter bodies 42, 60. Each of the adapters 112, 114 may optionally be capable of rotating or rolling the sheath body 42 and catheter body 60 relative to each other. If the working catheter 38 alternatively or additionally includes an operative element requiring mechanical actuation, the catheter adapter 114 may include additional spools (not shown) for tensioning control elements (not shown) coupled to the operative element.

The proximal ends of the electrical wires 84, 88 exit from the proximal end 62 of the catheter body 60 into the catheter adapter 114, which then exit the catheter adapter 114 as a bundle of wires that are terminated in an electrical connector 118. A radio frequency (RF) generator and electrophysiology mapping equipment (both not shown) can be coupled to the electrical connector 118 to allow the transmission of RF energy and temperature signals between the RF generator and the tip electrode 78 and temperature sensor 82 (shown in FIGS. 6 and 7), and to allow the transmission of signals between the ring electrode 80 (shown in FIGS. 6 and 7) and the electrophysiology mapping equipment. The proximal end of the fluid lumen 94 exits from the proximal end 62 of the catheter body 60 into the catheter adapter 114, which then exit the catheter adapter 114 and terminate in a luer connector 120. A fluid pump (not shown) can be coupled to the luer connector 120 to allow the conveyance of the fluid between the pump out through the fluid delivery ports 92 on the tip electrode 78 (shown in FIGS. 6 and 7). The proximal end of the push-pull rod 106 exits from the proximal end 62 of the catheter body 60 into the catheter adapter 114, which then exits the catheter adapter 114 and terminates in the force sensing assembly 40.

The force sensing assembly 40 comprises a mechanical ditherer 122 and a force sensor 124. Although only one force sensor 124 is shown and described, multiple force sensors can be used. In the illustrated embodiment, the ditherer 122 is mounted to the housing 110 of the instrument driver 34 proximal to the catheter adapter 114. The ditherer 122 is coupled to the proximal end of the push-pull rod 106, so that the push-pull rod 106 can be axially dithered back and forth, thereby axially dithering the distal end 64 of the catheter body 60 back and forth. The length or stroke of the dithering may be adjusted depending on the nature of the procedure, but generally is less than a few millimeters. In some embodiments, the stroke of the dithering may be less than about 1.5 mm. The frequency of the dithering may be several cycles per second, e.g., 10-20 Hz, thereby ensuring that any static friction is broken.

The force sensor 124 may be disposed at various locations, including at the distal end 64 of the catheter body 60. In the illustrated embodiment, the force sensor 124 is disposed on the ditherer 122. The force sensor 124 is used to detect the force or load that is being applied to the distal end 64 of the catheter body 60 by detecting the force or load that is applied at the proximal end of the push-pull rod 106. Thus, the force sensor 124 is able to sense the insertion and withdrawal forces applied to the distal end 64 of the catheter body 60 via the ditherer 122. The force sensing assembly 40 may optionally comprise a strain-gage (not shown) located at the distal end of the push-pull rod 106 for sensing lateral or deflection forces applied to the distal end 64 of the catheter body 60. The catheter 38 may also comprise a sensor, e.g., an optical or capacitive sensor (not shown), located at the distal end 64 of the catheter body 60 to confirm that the distal end 64 is dithering back and forth.

Figure 8:
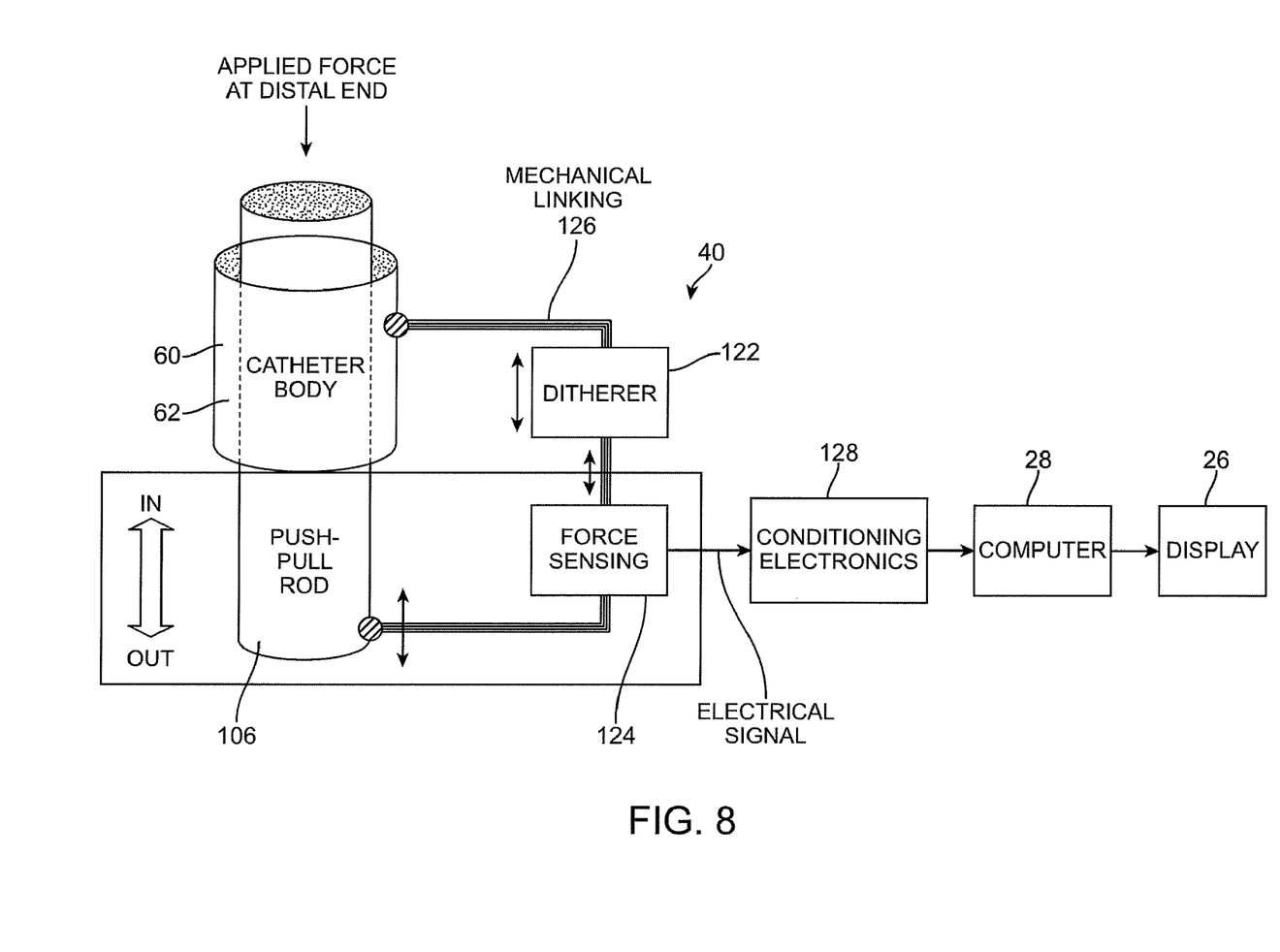
FIG. 8 is a conceptual view of a force sensing assembly used in the robotic catheter assembly of FIG. 2.

Turning now to FIG. 8, one embodiment of a force sensing assembly 40 used for measuring a force at the distal end 64 of the catheter body 60 will be described. In this embodiment, the distal end 64 of the catheter body 60 dithers with respect to the introducer sheath 36. In order to axially dither the distal end 64 of the catheter body 60 back and forth, the ditherer 122 will drive the push-pull rod 106 through the force sensor 124, which will measure the direct force needed to insert and retract the push-pull rod 106 within the lumen 104 of the working catheter 38. The ditherer 122 is mechanically grounded (via a mechanical linkage 126) to the proximal end 62 of the catheter body 60, and is thus, stationary relative to the introducer sheath 36. The force sensor 124 and push-pull rod 106 move together relative to the proximal end 62 of the catheter body 60.

The force sensing assembly 40 is in operable communication with control station 16 via the communication link 24 for data processing. In particular, condition electronics 128 receives the electrical signals generated by the force sensor 124, and the computer 28 processes the conditioned electrical signals. A representation of the axial force applied at the distal end 64 of the catheter body 60 can be displayed on the monitor 26.

Over one or more dithering cycles, the force profiles or waveforms obtained from the force signals can be used to accurately estimate the contact forces at the distal end 64 of the catheter body 60. In particular, the computer 28 obtains a baseline force measurement by receiving signals from force sensor 124 when the push-pull rod 106 is dithered back and forth and while an external axial force is not applied to the distal end 64 of the catheter body 60. The computer 28 may then later obtain a total force measurement by receiving signals from the force sensor 124 when the push-pull rod 106 is dithered back and forth and an external axial force is applied to the distal end 64 of the catheter body 60 (e.g., when the distal tip of the catheter 38 contacts tissue). The computer 28 then computes the external axial force applied to the distal end 64 of the catheter body 60 by subtracting the baseline force measurement from the total force measurement. Notably, the total force measurement may capture signal induced by physiological cycles, such as the respiratory cycle and heart cycle. To interpret this signal, such as for control purposes, the force sensing assembly 40 may comprise a filter (not shown) for separating the physiological variations within the total force measurement.

Further details on this type of force sensor system, along with various other embodiments of dithering force sensor assemblies, are provided in U.S. patent application Ser. No. 11/678,001, which has previously been incorporated herein by reference.

Figure 9A:
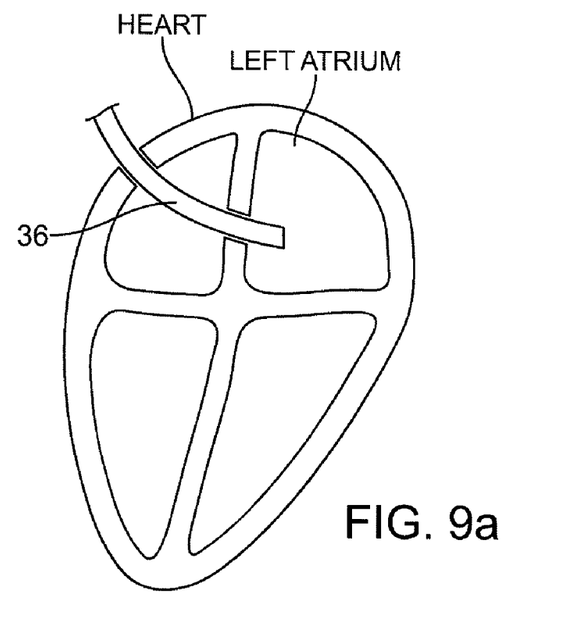
FIG. 9 illustrates a method of operating the robotic catheter system of FIG. 1 to sense a force applied between endocardial tissue and the distal end of the working catheter illustrated in FIG. 6.
Figure 9B:
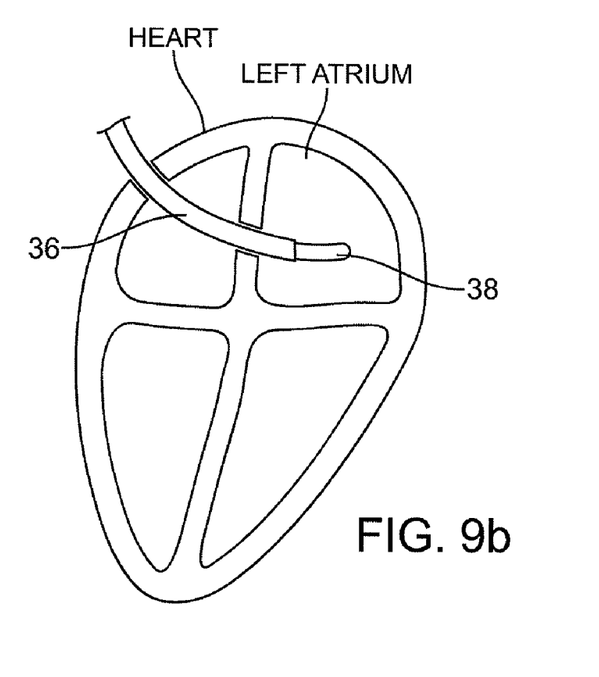

Having described the robotic catheter system 10, one exemplary method of using the robotic catheter system 10 to perform therapeutic and/or diagnostic functions on a patient will now be described. First, the introducer sheath 36, with the working catheter 38 retracted therein, is intravascularly introduced through a puncture within the patient's body and robotically advanced through the vasculature of the patient to a target site, such as a chamber of the heart, as illustrated in FIG. 9a. In this case, the introducer sheath 36 is transeptally introduced into the left atrium of the heart. The working catheter 38 is then robotically advanced out of the introducer sheath 36, as shown in FIG. 9b. The distal end of the working catheter 38 is then axially dithered back and forth relative to the proximal end of the working catheter 38, as shown by the arrows in FIG. 9c. In the illustrated embodiment, this is accomplished by operating the ditherer 122 to axially dither the push-pull rod 106 back and forth, thereby dithering the distal end of the working catheter 38 back and forth via operation of the bellows 70.

Figure 9C:
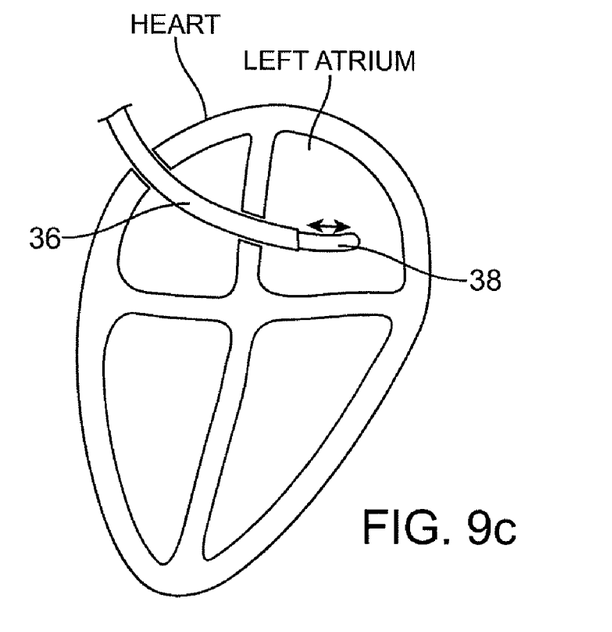
Figure 9D:
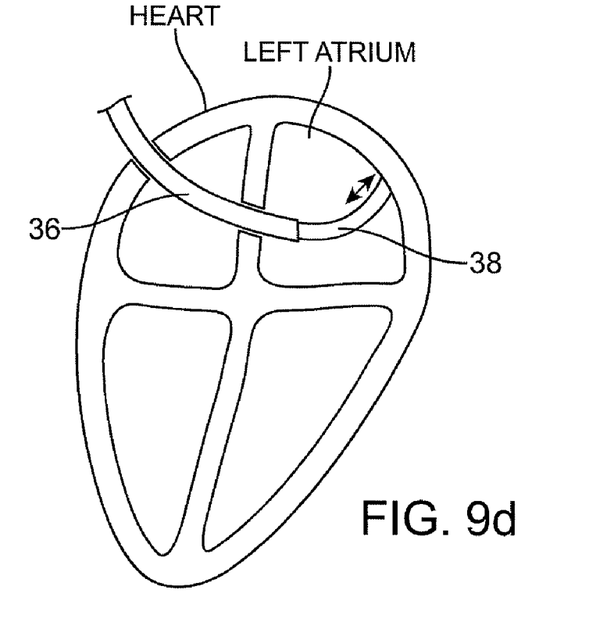

Preferably, as shown in FIG. 9c, the distal end of the working catheter 38 is axially dithered back and forth when an external axial force is not presently applied between the tissue and the distal end of the working catheter 38, and measuring the force at the force sensor 124 to obtain a baseline force measurement. While the distal end of the working catheter 38 is dithered, it is then robotically moved within at least one-degree of freedom (e.g., by deflecting the distal end of the working catheter 38), thereby placing it in contact with tissue, as shown in FIG. 9d. Because the force at the force sensor 124 is continuously measured, the total force measurement will be obtained as the distal end of the working catheter 38 is placed into contact with the tissue. The axial force applied between the tissue and the distal end of the working catheter 38 can then be computed (in this case, by the computer 28) by subtracting the baseline force measurement from the total force measurement.

The operative elements at the distal end of the working catheter 38 (in this case, the tip ablation electrode 78 and mapping ring electrode 80) can then be operated to perform the therapeutic and/or diagnostic function (in this case, tissue ablation and/or mapping) on the patient. The distal end of the working catheter 38 can be moved to a different region on the tissue. The axial force applied between the tissue and the distal end of the working catheter 38 can again then be measured and the operative elements at the distal end of the working catheter 38 operated to again perform the therapeutic and/or diagnostic function.

Figure 10:
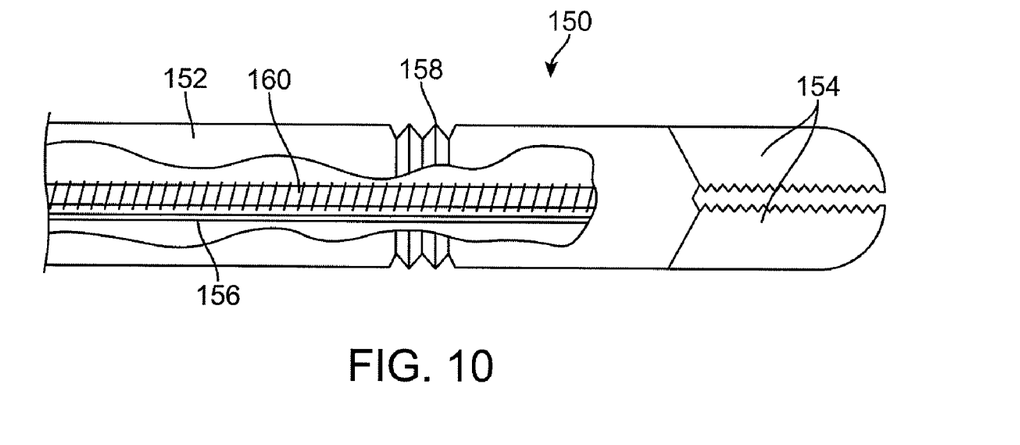
FIG. 10 is a plan view of the distal end of another working catheter used in the robotic catheter assembly of FIG. 2.

As briefly discussed above, the force sensing mechanism disclosed herein and be used with medical devices with operative elements other than ablation/mapping electrodes. For example, operative elements, such as energy delivering laser fibers, scalpel, grasper/tweezers; sensor (radiometer, IR, spectrometer (excitation light source in combination with a detector)), etc., can be used. For example, FIG. 10 illustrates a working catheter 150 having an elongated catheter body 152, a pair of grasper arms 154 affixed to the distal end of the catheter body 152, and a cable 156 extending through the catheter body 152 and coupled to the grasper arms 154.

The grasper arms 154 can be spring-loaded to open relative to each other, in which case, the cable 156 can be pulled to close the arms 154 relative to each other. As with the working catheter 38, the working catheter 150 includes an axially flexible section 158, and a push-pull rod 160 slidably disposed within a central lumen 162 extending through the catheter body 152. The distal end of the push-pull rod 160 is affixed to the catheter body 152 at a point distal to the axially flexible section 158, and in particular, to the distal end of the catheter body 150, and a proximal end that extends out from the proximal end of the catheter body 152, so that it can be suitably coupled to the force sensing assembly 40 in the manner discussed above. As with the catheter 38, the catheter 150 optionally comprises a centering coil 162 affixed around the push-pull rod 160.

Figure 11:
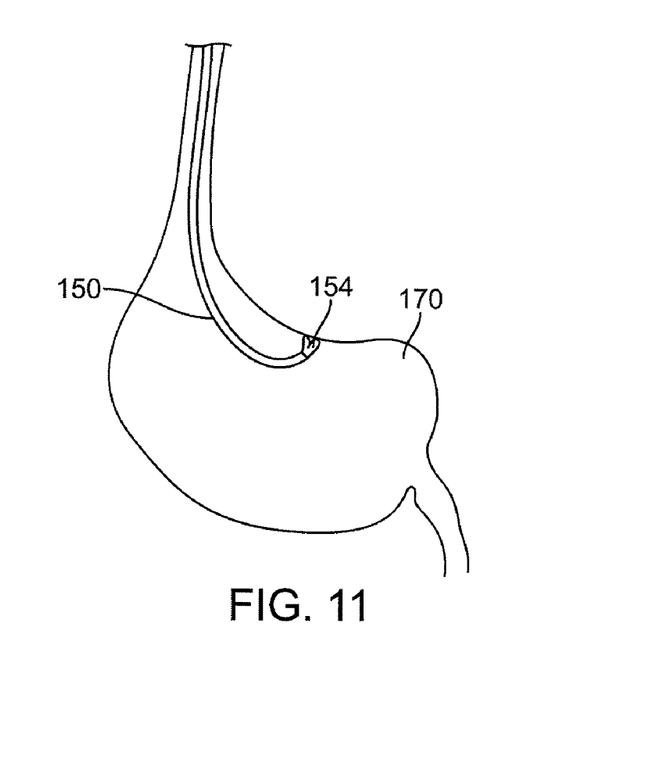
FIG. 11 illustrates a method of operating the robotic catheter system of FIG. 1 to sense a force applied between the inner lining of a stomach and the distal end of the working catheter illustrated in FIG. 10.

The force sensing mechanism disclosed herein can be used to perform medical procedures in anatomical regions other than the heart. For example, as shown in FIG. 11, the working catheter 150 can be used to perform a surgical procedure within the cavity of the stomach 170 while sensing the force between the grasper arms 154 and the wall of the stomach to prevent perforation of the inner lining of the stomach.

Although the previous embodiments have been described as having axially flexible sections, such as bellows, so that the proximal and distal sections of the catheter body can be axially displaced relative to each other in response to the application of an axial force to the distal section of the probe body, other types of axially translatable sections can be used to perform this function.

Figure 12:
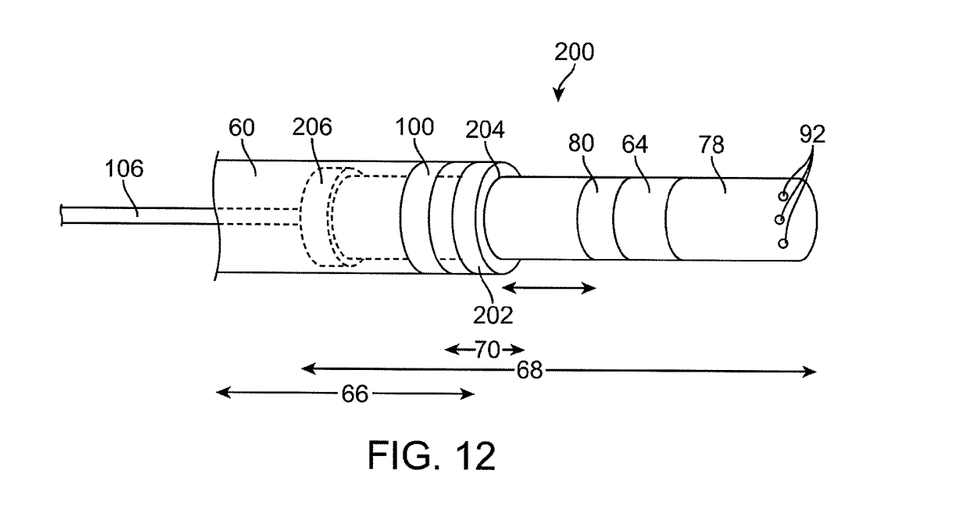
FIG. 12 is a perspective view of the distal end of still another working catheter used in the robotic catheter assembly of FIG. 2.

For example, referring to FIG. 12, a working catheter 200 is similar to the working catheter 38, with the exception that instead of an axially flexible section (e.g., an bellows), the working catheter 200 includes an axially translatable section 70 that has a seal 202 suitably mounted to the distal end of the proximal shaft section 66. The seal 202 includes an annular aperture 204 through which the distal shaft section 68 is disposed. The diameter of the aperture 204 is equal to or less than the outer diameter of the distal shaft section 68. Thus, the distal shaft section 68 is slidably disposed within the proximal shaft section 66 via the seal 202, which prevents bodily fluids, such as blood, from entering the working catheter 200 via the interface between the proximal and distal shaft sections 66, 68. The distal end of the push-pull rod 106 is affixed to the distal shaft section 68, and thus, is displaced with the distal shaft section 68 in the manner and with the result described above with respect to the working catheter 38.

The seal 200 may be composed of a suitable material, such as rubber, to allow the proximal and distal shaft sections 66, 68 to easily slide relative to the each other while maintaining a good seal therebetween. The proximal end of the distal shaft section 68 preferably includes an annular flange 206 that abuts the seal 202 during the farthest extent of distal shaft section 68, thereby preventing the distal shaft section 68 from disengaging from the proximal shaft section 66. In alternative embodiments, the seal 202 is suitably mounted to the proximal end of the distal shaft section 68, in which case, the proximal shaft section 66 will be slidably disposed within the distal shaft section 68 via the seal 202.

Figure 13:
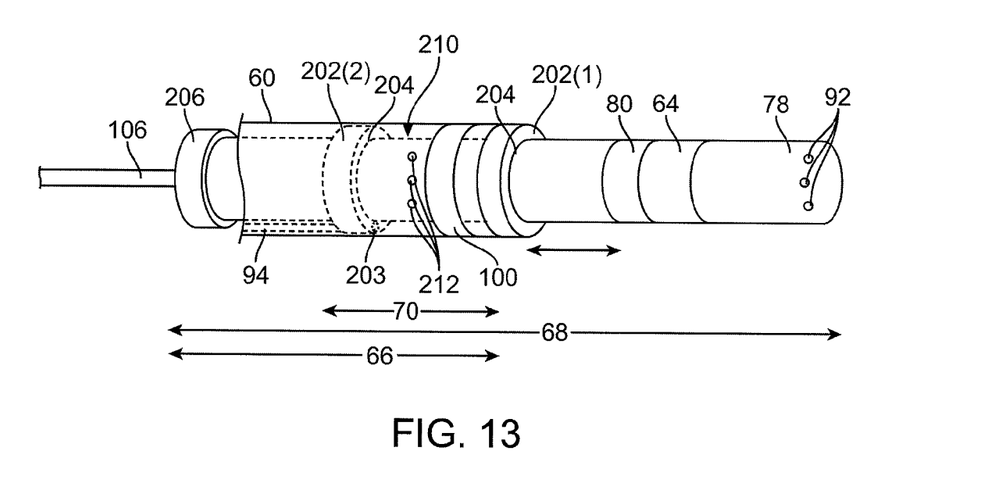
FIG. 13 is a perspective view of the distal end of yet another working catheter used in the robotic catheter assembly of FIG. 2.

In an alternative embodiment illustrated in FIG. 13, the working catheter 200 includes a pair of seals 202—one seal 202(1) mounted to the distal end of the proximal shaft section 66, and another seal 202(2) mounted within the proximal shaft section 66 proximal to the first seal 202(1). Each of the seals 202 includes an annular aperture 204 through which the distal shaft section 68 is disposed. Thus, the seals 202 provide suitable bearing surfaces that maintain axial alignment of the distal shaft section 68 within the proximal shaft section 66. In this embodiment, the distal end of the fluid lumen 94 extending through the catheter body 60 terminates in an aperture 208 within the proximal seal 202(2). Thus, fluid can be conveyed into a chamber 210 formed between the seals 202, thereby creating a positive pressure therein. As a result, any bodily fluids, such as blood, that would otherwise leak through the distal seal 202(1) is prevented from entering the working catheter 200 due to the positive pressure. Furthermore, apertures 212 are formed in the distal shaft section 68 through which the positively pressurized fluid can be conveyed to the irrigation ports 92 on the electrode 78 to provide the irrigation function described above.

While multiple embodiments and variations of the many aspects of the invention have been disclosed and described herein, such disclosure is provided for purposes of illustration only. Many combinations and permutations of the disclosed system are useful in minimally invasive surgery, and the system is configured to be flexible. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, it should be understood that the invention generally, as well as the specific embodiments described herein, are not limited to the particular forms or methods disclosed, but also cover all modifications, equivalents and alternatives falling within the scope of the appended claims.

What is claimed is:

1. A medical system, comprising:
a medical probe including an elongated probe body having a proximal section, a distal section, and an axially translatable section disposed between the proximal and distal sections, a lumen axially extending within the probe body, and a push-pull rod slidably disposed within the lumen, the push-pull rod having a distal end that is affixed to the distal section of the probe body and a proximal end slidable within and extending from the proximal section of the probe body;
a dithering mechanism mechanically coupled to the proximal end of the push-pull rod, the dithering mechanism configured for cyclically displacing the push-pull rod axially back and forth within the lumen within the probe body, such that the displacement of the push-pull rod causes the distal section of the probe body to be axially dithered back and forth relative to the proximal section of the probe body via the axially translatable section of the probe body; and
at least one sensor configured for sensing an external force axially applied to a distal tip of the probe body.

2. The medical system of claim 1, wherein the probe body is an intravascular catheter body.

3. The medical system of claim 1, wherein the axially translatable section of the probe body comprises an axially flexible member.

4. The medical system of claim 3, wherein the axially flexible member is a bellows.

5. The medical system of claim 1, wherein the axially translatable section of the probe body comprises at least one seal that allows one of the proximal and distal sections of the probe body to slide within the other of the proximal and distal sections of the probe body.

6. The medical system of claim 1, wherein the medical probe further includes an operative medical element mounted to the distal tip of the probe body.

7. The medical system of claim 1, wherein the medical probe further comprises a coil wrapped around the push-pull rod, the coefficient of friction between the coil and the lumen being less than the coefficient of friction between the push-pull rod and the lumen.

8. The medical system of claim 1, wherein the at least one sensor is mounted on the dithering mechanism.

9. The medical system of claim 1, further comprising a drive mechanism affixed to the proximal section of the probe body for effecting movement of the probe body within at least one degree of freedom.

10. The medical system of claim 9, wherein the medical probe further includes at least one control element extending within the probe body, and wherein the drive mechanism includes an adapter coupled to the at least one control element for deflecting the distal tip of the probe body in at least one direction.

11. The medical system of claim 10, wherein the at least one control element is affixed to the probe body at a point proximal to the axially translatable section.

12. The medical system of claim 9, wherein the proximal end of the push-pull rod is configured for being axially displaced by the dithering mechanism relative to the drive mechanism.

13. The medical system of claim 9, further comprising an introducer sheath having a lumen in which the probe body is disposed, wherein the drive mechanism is configured for axially displacing the probe body and the introducer sheath relative to each other.

14. The medical system of claim 1, further comprising a computer configured for obtaining a baseline force measurement by receiving signals from the at least one sensor when the push-pull rod is dithered back and forth without an external axial force applied to the distal tip of the probe body, for obtaining a total force measurement by receiving signals from the at least one sensor when the push-pull rod is dithered back and forth with an external axial force applied to the distal tip of the probe body, and computing the external axial force applied to the distal tip of the probe body by subtracting the baseline force measurement from the total force measurement.

* * * * *